United States Patent [19]

Stele

[11] 4,189,837
[45] Feb. 26, 1980

[54] DENTAL JAW SIMULATOR

[76] Inventor: Aaron Stele, 10 Beechwood Ter., W. Orange, N.J. 07052

[21] Appl. No.: 809,297

[22] Filed: Jun. 23, 1977

[51] Int. Cl.² ............................................. A61C 11/00
[52] U.S. Cl. ........................................ 433/57; 433/59; 433/60; 433/67
[58] Field of Search ............................................. 32/32

[56] References Cited

U.S. PATENT DOCUMENTS

| | | | |
|---|---|---|---|
| 1,338,918 | 5/1920 | Hall | 32/32 |
| 1,368,408 | 2/1921 | Needles | 32/32 |
| 1,815,956 | 7/1931 | Ralph | 32/32 |
| 2,204,809 | 6/1940 | Miller et al. | 32/32 |
| 2,592,288 | 4/1952 | Johnson | 32/32 |
| 2,608,761 | 9/1952 | Scott | 32/32 |
| 2,786,272 | 3/1957 | Lindley | 32/32 |
| 3,159,915 | 12/1964 | Ben et al. | 32/32 |
| 3,815,242 | 6/1974 | Martfay et al. | 32/32 |

*Primary Examiner*—Louis G. Mancene
*Assistant Examiner*—John J. Wilson

*Attorney, Agent, or Firm*—Lerner, David, Littenberg & Samuel

[57] ABSTRACT

A dental jaw simulator is provided for duplicating human jaw movements and, in particular, the movement of the lower human jaw. The simulator includes a support frame and an upper jaw member pivotally mounted on the support frame and which is adapted to receive an upper dental arch cast. A lower jaw member is also mounted on the support frame and is adapted to receive a lower dental arch cast. Movement of the lower jaw member in protrusive and retrusive directions and in a lateral direction is controlled by a ball and slot hinge arrangement in combination with a movable anterior platform mounted on the support frame and a forward pin connected to the lower jaw member and which engages and is movable relative to the anterior platform. The anterior platform is provided with sloping planes on which the forward pin moves to guide the lower jaw member in order to duplicate the dropping of the lower human jaw during lateral movement.

18 Claims, 6 Drawing Figures

DENTAL JAW SIMULATOR

FIELD OF THE INVENTION

The present invention relates generally to dental jaw simulators and to an improved jaw simulator which accurately duplicates the movement of the human jaw and, in particular, the movement of the lower human jaw.

BACKGROUND OF THE INVENTION

Dental articulators are well known in the prior art and are generally used for two purposes. First, as a diagnostic and planning instrument and second, for the technical procedures in constructing prostheses and other restorative appliances. Such restorative appliances typically include full upper and lower dentures, partial dentures, or complete mouth bridge work. In fact, all such restorative appliances are constructed on such dental articulators.

Typically, dental articulators are designed such that the upper half of the instrument, on which is mounted the upper dental arch cast, is movable laterally and back and forth in an attempt to duplicate the movements of the human jaw. These jaw movements which must be duplicated include the retruded contact position, the intercuspal position, as well as the protruded and lateral positions. However, in most of the prior art articulators, these movements of the human jaw are re-created or duplicated inaccurately. This results from the fact that the upper jaw member of the articulator is movable, and the lower jaw member is stationary, whereas in the human jaw, the reverse is true. That is, in the human jaw, the upper jaw is stationary, whereas the lower jaw experiences the protrusive and retrusive movement, as well as lateral movement, about the temporomandibular joint. Therefore, the restorative appliances which are constructed on such dental articulators simulate movement of the mouth in a manner opposite to the actual movement of the mouth so that all registrations are being transposed incorrectly, and the movements of the lower human jaw and the temporomandibular joints are recreated or duplicated inaccurately on such dental articulators.

It is known that the lower human jaw experiences protrusive and retrusive movement, as well as movement in lateral directions from a vertical axis which may be referred to as the centric axis. As the lower human jaw moves to either side of the centric axis, it is moving not only laterally but also downwardly with respect to the upper human jaw. This lateral and downward movement of the lower jaw is caused by the intercuspal engagement of the upper and lower posterior teeth. Accordingly, in order for a dental articulator to accurately duplicate human jaw movements, and in particular, the movement of the lower human jaw in the lateral direction, the articulator must be constructed to simulate all these directions of movement of the lower human jaw which include protrusive and retrusive movement and lateral movement, with the lateral movement being downwardly as the lower jaw moves laterally with respect to the centric axis.

Although prior art articulators have been developed in which the lower jaw portion is movable, the mechanics employed do not accurately simulate the actual movements of the lower human jaw. For example, such articulators do not provide means for mechanically duplicating the dropping of the lower human jaw relative to the upper jaw during lateral movement of the lower jaw.

Broadly, it is an object of the present invention to provide an improved jaw simulator which overcomes one or more of the aforesaid problems. Specifically, it is within the contemplation of the present invention to provide a dental jaw simulator which accurately duplicates the movement of the human jaw and, in particular, the movement of the lower human jaw.

It is a further object of the present invention to provide an improved jaw simulator which accurately duplicates the lateral and downward movement of the lower human jaw as it is moved from side to side with respect to the centric axis.

It is a still further object of the present invention to provide an improved jaw simulator which includes an anterior platform having a plurality of different planes for accurately duplicating the dropping of the lower human jaw during lateral movement.

SUMMARY OF THE INVENTION

Briefly, in accordance with the principles of the present invention, an improved dental jaw simulator is provided for duplicating human jaw movements and, in particular, the movement of the lower human jaw. The simulator includes a support frame and an upper jaw member pivotally mounted on the support frame which is adapted to receive an upper dental arch cast. In addition, a lower jaw member is mounted on the support frame and is adapted to receive a lower dental arch cast. The upper and lower dental arch casts are similar in that they each include a plastic tray removably connected to the support frame and mounting plaster which is set in the plastic tray. The denture or other appliance is then supported on the mounting plaster.

The upper jaw member is pivotally mounted on the support frame so that it can be pivoted upwardly and away from the lower jaw member to allow work to be performed on the upper dental arch cast and the lower dental arch cast without interference with each other. To make the necessary registrations and adjustments of the teeth on the upper and lower casts, the present invention provides means for moving the lower jaw member in protrusive and retrusive directions and in a lateral direction. These means include a ball and slot hinge arrangement which operates in combination with a movable anterior platform mounted on the support frame and a forward pin member connected to the lower jaw member and which engages and is movable relative to the anterior platform. The anterior platform is provided with a flat plane and a plurality of sloping planes on which the forward pin member moves to guide the lower jaw member in order to accurately duplicate the dropping of the lower human jaw during lateral movement.

The protrusive and retrusive movement of the lower jaw member is controlled by the ball and slot hinge arrangement in combination with the forward pin member being moved back and forth on the anterior platform. To duplicate the lateral movement of the lower jaw of the patient, it is necessary to determine the degree of intercuspal engagement of the upper and lower posterior teeth of the patient. More particularly, in younger patients where the posterior teeth have not been worn down substantially, the intercuspal engagement of the upper and lower posterior teeth is greater than in those cases where the posterior teeth have been worn down, such as in older patients. Therefore, in accordance with the present invention, the anterior platform is provided with a plurality of sloping planes which may be, for example, 0° (a flat plane), 10°, 20°, or 30°. In this manner, where there is a high degree of intercuspal engagement, then the anterior platform having a 20° or 30° sloping plane will be utilized in combination with the present jaw simulator in order to most accurately duplicate the dropping of the lower jaw of the patient during lateral movement. However, it is typical with older patients that the intercuspal engagement of the posterior teeth is very small or nonexistent. In such cases, the present jaw simulator would employ the anterior platform having a 0° flat plane or 10° sloping plane to most accurately duplicate the lateral jaw movement of such a patient.

In addition, in accordance with the present invention, interchangeable plastic trays are employed in the upper and lower jaw members. Such plastic trays are provided with removable engagement means for removably supporting the mounting plaster of the upper and lower dental arch casts. In this manner, the mounting plaster and the denture which it supports may be removed from the plastic tray by simply removing the engagement means which holds the mounting plaster in engagement with the plastic tray. In this manner, the mounting plaster and denture may be readily removed from the dental jaw simulator without necessitating the removal of the plastic tray.

BRIEF DESCRIPTION OF THE DRAWINGS

Further objects, features, and advantages of the present invention will become apparent upon the consideration of the following detailed description of a presently-preferred embodiment when taken in conjunction with the accompanying drawings, wherein.

DETAILED DISCUSSION OF THE PREFERRED EMBODIMENT OF THE INVENTION

Figures 1, 1A:
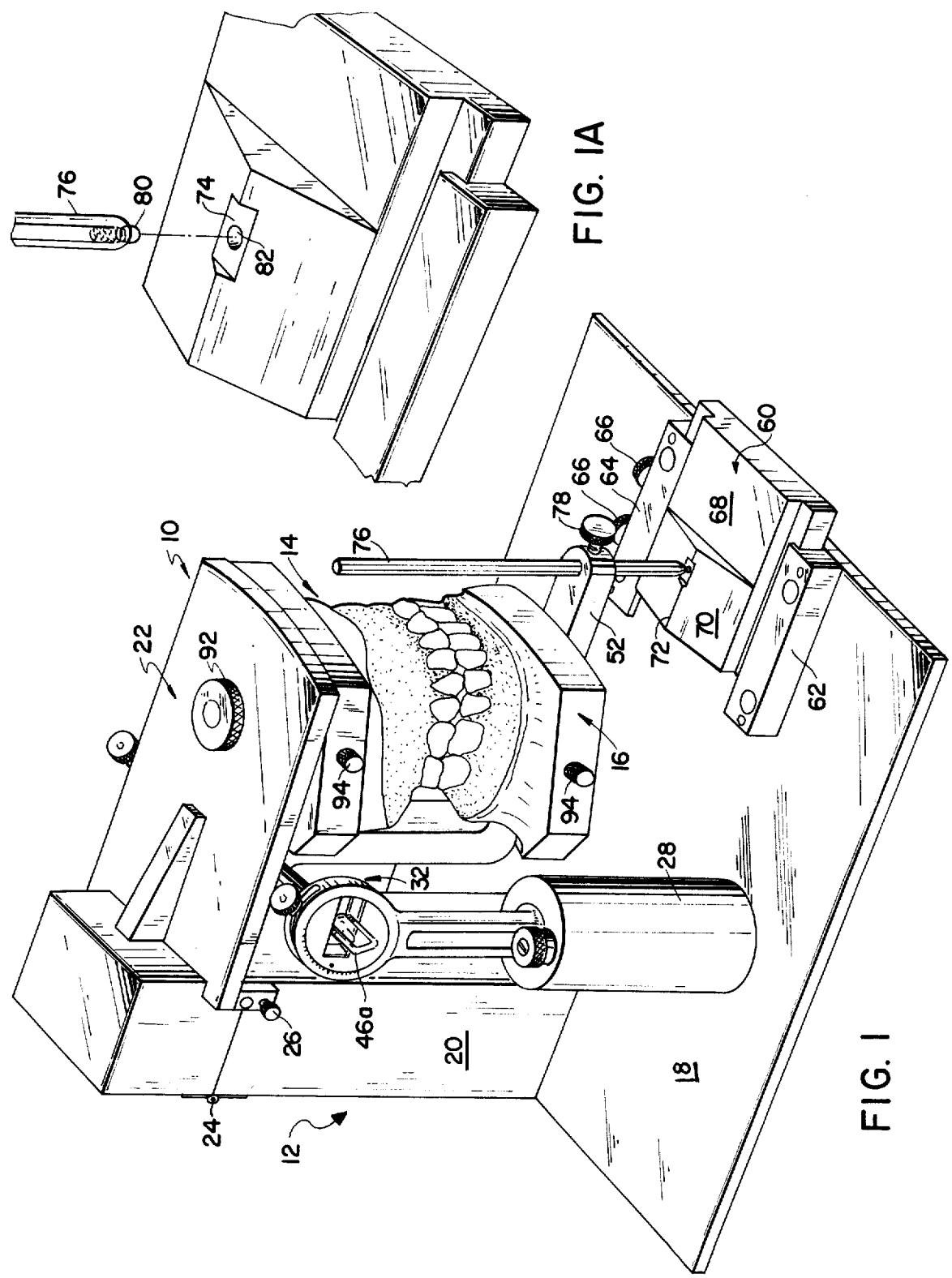
FIG. 1 is a perspective view of a dental jaw simulator embodying the principles of the present invention.
FIG. 1a is a detailed view of a portion of the anterior platform and forward pin member illustrated in FIG. 1.
Figure 2:
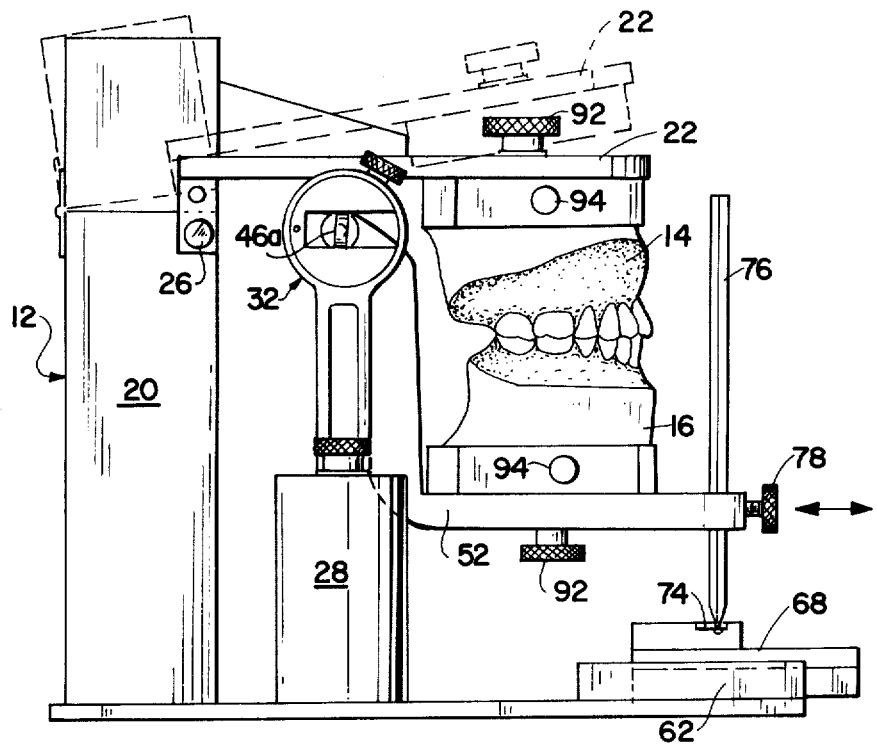
FIG. 2 is a side elevational view of the dental jaw simulator shown in FIG. 1.
Figure 3:
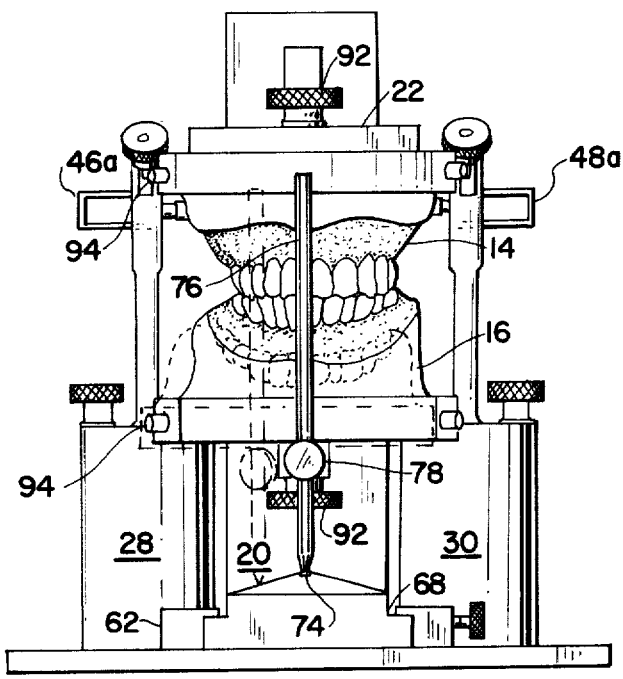
FIG. 3 is a front elevational view of the simulator, illustrating in dotted lines the lateral movement of the lower jaw member to the left of the centric axis.

Referring now to FIG. 1, there is shown an improved dental jaw simulator embodying the principles of the present invention, generally designated by the reference numeral 10, which includes a support frame 12, an upper jaw member 14 mounted on the support frame 12, and a lower jaw member 16 also mounted on the support frame 12.

The support frame 12 includes a base member 18 on which is mounted a vertical post 20 to which is pivotally connected a horizontally-extending support member 22 for supporting upper jaw member 14 on support frame 12. Support member 22 is pivotally mounted on vertical post 20 about hinge axis 24. In this manner, when work on the upper or lower jaw members 14, 16 is necessary, the support member 22 is pivoted to its open position, so that the upper or lower jaw members may be worked on without interference from each other. However, when it is desired to simulate the movement of the lower jaw member 16 relative to the upper jaw member 14, upper jaw member 14 is locked in position relative to vertical post 20 by locking screws 26.

Figure 5:
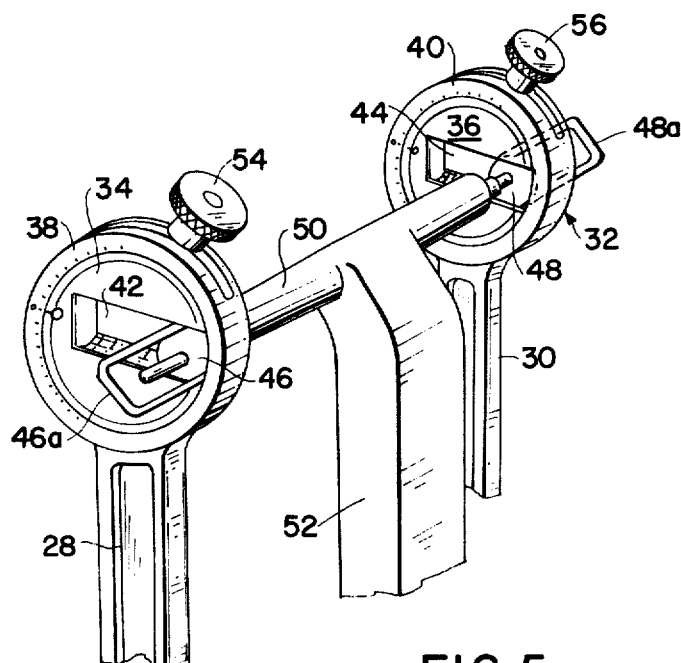
FIG. 5 is a detailed perspective view of the ball and slot hinge arrangement of the dental jaw simulator illustrated in FIG. 1.

Also mounted on base member 18 are hinge supports 28, 30 for supporting the ball and slot hinge arrangement generally designated as 32 and which is shown in detail in FIG. 5. As shown in FIG. 5, the ball and slot hinge arrangement 32 includes rotatable inner members 34, 36 which are mounted to rotate within respective circular housing members 38, 40 having indicia means for indicating the angular position of inner members 34, 36. The rotatable inner members 34, 36 include respective cutout portions or slots 42, 44 in which respective ball members 46, 48 are mounted for universal movement. The ball members 46, 48 are mounted on the ends of a pivoting axis member 50 which is fixedly connected to an L-shaped support member 52 on which is mounted lower jaw member 16. Axis member 50 is located relative to the upper and lower jaw members 14, 16 to duplicate the position of the human temporomandibular joint relative to the human jaw.

For a purpose to be explained, the ends of axis member 50 are provided with U-shaped locking sleeves 46a, 48a which are threaded onto the ends of axis member 50. Locking sleeves 46a, 48a may be threaded along axis member 50 a sufficient distance so that they will engage and surround respective ball members 46, 48 and prevent their movement along respective slots 42, 44, when desired.

As will be understood from FIGS. 1 and 5, lower jaw member 16 is moved in a protrusive and retrusive direction by moving L-shaped support member 52 and ball members 46, 48 back and forth within respective slots 42, 44 of hinge arrangement 32. In addition, inner members 34, 36 may be rotated to any desired angle relative to housing members 38, 40 to duplicate the position of the lower jaw member 16. Locking screws 54, 56 are provided for locking inner members 34, 36 at the selected angle.

Turning now to FIGS. 1 and 1a, there is shown a movable anterior platform 60 slidably mounted on base member 18 of support frame 12. The anterior platform 60 is slidably mounted in guides 62, 64 which are provided with a pair of locking screws 66 for locking platform 60 in the selected position. As will be seen from the drawings, anterior platform 60 includes a flat plane 68 in front of and adjacent to a pair of sloping planes 70 which meet at a crest 72 in the center of platform 60. The sloping planes 70 are at an angle with respect to the flat plane 68, for a purpose to be described, and such angle may be in the range of 10°, 20°, or 30°. Moreover, in accordance with the present invention, a plurality of different platforms 60 may be employed, each having sloping planes of a different angle. In this manner, depending on the degree of the patient's intercuspal engagement, the desired platform 60 may be selected and positioned within guides 62, 64. Accordingly, platforms 60 may be interchangeable, or alternatively, one platform can be provided with a plurality of sloping planes, each being at an angle of 10°, 20°, and 30°.

As shown most clearly in FIG. 1a, the central crest portion 72 of the anterior platform 60 is provided with a trough or flat portion 74 for guiding the protrusive and retrusive movement of a forward pin member 76 relative to platform 60. The pin member 76 is adjustably mounted in the end of L-shaped support member 52, and a locking screw 78 is provided to lock the forward pin member 76 in the adjusted or desired centric opening position. The bottom end of pin member 76 is provided with a spring-biased ball member 80 which is adapted to engage a recess 82 formed in trough 74. To duplicate the occlusal position, with the lower teeth being in engagement with the upper teeth, locking screw 78 is loosened, and forward pin member 76 is adjusted relative to L-shaped support member 52 until the upper and lower teeth are in engagement and ball member 80 of pin member 76 is engaged within recess 82. Once this occlusal position is duplicated, locking screw 78 is tightened so that forward pin member 76 operates to hold the lower jaw member 16 in engagement with the upper jaw member 14. Then, in order to duplicate the rest position of the lower human jaw, in which the upper and lower teeth are slightly out of engagement with each other, it is only necessary to push down on L-shaped support member 52 and forward pin member 76 to compress ball member 80 against the spring within forward pin member 76. In this manner, the lower jaw member 16 will drop down a small distance relative to the upper jaw member and thereby accurately duplicate the rest position of the lower human jaw.

Figure 4:
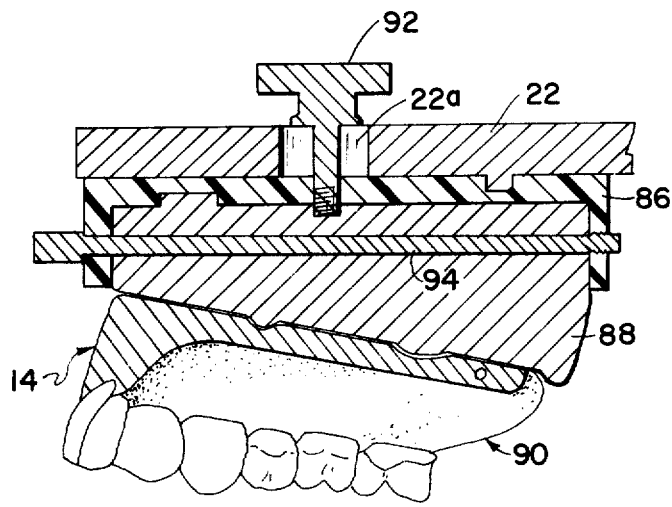
FIG. 4 is a detailed view of the upper jaw member removed from the support frame.

Referring now specifically to FIG. 4, there is shown in detail the construction of the upper jaw member 14 which, it should be noted, is essentially identical to the lower jaw member 16, which is the mirror image thereof. Upper jaw member 14 is supported on horizontal support member 22 and includes an interchangeable tray 86 formed of plastic or other suitable material for receiving mounting plaster 88 which provides an impression of the patient's mouth and gums. As is well known in the art, mounting plaster 88 is adapted to support thereon the restorative appliance being constructed, such as a denture 90. Horizontal support member 22 includes a locking screw 92 which is adapted to engage and removably mount tray 86 on the support frame 12. In this manner, the tray 86 and denture 90 for one patient may be removed from the simulator 10 and replaced with the appliance of another patient, so that it can be worked on using the same simulator. Advantageously, the appliances for any number of patients may be worked on utilizing the same simulator 10 and thereby avoids the need of a simulator for each patient being worked on. As may also be seen in FIG. 4, locking screw 92 is adjustable along a slot 22a so that tray 86 and denture 90 may be set in the desired position relative to axis 50 to compensate for such conditions as overbite and the like. The locking screw for the lower jaw member is similarly adjustable. In this manner, the present jaw simulator can be adjusted over a wide range to duplicate all types of jaw conditions. In addition, while working on a particular appliance or denture 90, it may be necessary to remove the mounting plaster 88 and denture 90 temporarily to perform various operations on it and then replace it within the articulator. In order to provide means for quickly removing the appliance 90 and mounting plaster 88 from tray 86, a sliding handle 94 is provided. In this manner, to remove mounting plaster 88 and denture 90 from plastic tray 86, it is only necessary to remove the sliding handle 94 from engagement with the walls of the plastic tray 86 and the mounting plaster 88. As a result, the denture 90 and mounting plaster 88 may be quickly removed from tray 86 so that work may be performed on it. Of course, the appliance may be reinstalled within the plastic tray 86 by simply sliding handle 94 through the mounting plaster 88 and walls of tray 86. In this manner, it is not necessary to unthread locking screw 92 and remove the entire interchangeable tray 86 from the simulator when various operations are to be performed on the appliance. It may be necessary to do this when it is desired to remove the patient's appliance and tray 86 for supporting same in order to provide easier handling and transport.

In order to provide a complete understanding of the present invention, there will now be provided a brief description of the operation of the jaw simulator of the present invention. Initially, as is well known in the art, in order to prepare, for example, upper and lower dentures for a patient, impressions are taken of the upper and lower jaws of the patient. From this, a temporary plate is made to fit the patient's mouth and to provide the required registrations. These measurements or registrations include the centric opening, which establishes the height of the teeth; the median line; the lip line; and the cuspal position. These registrations or measurements are supplied to the dental technician who uses these measurements to construct the denture on the simulator. First, the casts or impressions 88 are mounted on plastic trays 86, and the dental technician uses the registrations provided by the dentist to start setting up the teeth in wax. Preferably, all the upper teeth are set up first to form the upper denture 90. A median occlusal plane (not shown) is then mounted on forward pin member 76 to ensure that the surfaces of the upper teeth are all in the same flat plane, which is perpendicular to forward pin member 76. Once the work has been completed on the upper denture 90, the horizontal support member 22 is left in the open position so that work can be performed on lower jaw member 16. The forward pin member 76 is utilized to establish the centric opening for the lower teeth. In setting up the lower teeth, it is preferable for the dental technician to first set up the anterior teeth and then the posterior teeth. Again, the median occlusal plane is mounted on pin member 76 to establish that the upper surfaces of the lower teeth are all in the same plane which is perpendicular to the pin member 76.

Once all of the upper and lower teeth have been set up on the upper and lower jaw members 14, 16, the horizontal support member 22 is pivoted to its closed position about hinge axis 24 so that upper jaw member 14 is brought into contact or close engagement with lower jaw member 16. To hold the upper jaw member in a fixed position, locking screws 26 on each side of vertical post 20 are tightened. Then, locking screws 54, 56 of the hinge arrangement 32 are loosened, and locking screw 78 is also loosened so that pin member 76 is movable relative to the support member 52. Next, sleeves 46a, 48a are tightened relative to ball members 46, 48 to prevent the ball members from moving along slots 42, 44 when the occlusal position is being established. In this manner, the lower jaw member 16 is moved relative to the upper jaw member 14 so that the upper and lower teeth are brought into intercuspal engagement. While holding the lower jaw member 16 in this position, the forward pin member 76 is moved relative to support member 52 so that the lower end or ball member 80 of the forward pin member 76 is brought into contact with recess 82. Locking screw 78 is then tightened to hold pin member 76 in this position which establishes the occlusal position. In addition, locking screws 54, 56 are tightened to maintain inner members 34, 36 at their selected angular position.

Then, to duplicate movement of the lower jaw member 16 in the protrusive and retrusive directions, sleeves 46a, 48a are loosened, pin member 76 is moved back and forth within trough 74, and axis member 50 and ball members 46, 48 are now free to slide within slots 42, 44. In this manner, as the lower jaw member is moved in the protrusive and retrusive directions, it can be determined if there is any interference between the upper and lower teeth, and any necessary adjustments can be performed.

Then, in order to duplicate the lateral movement of the lower jaw of the patient, pin member 76 is moved to the left and right of crest 72 and along the sloping planes 70, with ball member 80 riding on such sloping planes. In this manner, as the pin member 76 traces the sloping planes 70, the lower jaw member 16 will drop slightly relative to the upper jaw member 14 as it moves laterally in either direction. As a result, the hinge arrangement 32, in combination with the sloping planes 70 and pin member 76, operates to accurately duplicate the dropping of the lower human jaw during lateral movement thereof. It will be understood that as pin member 76 rides along sloping planes 70, that ball members 46, 48 of hinge arrangement 32 will move and pivot within respective slots 42, 44.

It should also be understood that the sloping planes 70 can be provided at the desired angle which most closely duplicates the movement of the patient's lower jaw. For example, in younger patients who have greater intercuspal engagement of the upper and lower teeth, sloping planes 70 having an angle of 20° or 30° would be selected and utilized within guides 62, 64. However, in older patients who have a smaller degree of intercuspal engagement, the sloping planes may have an angle of only 10°. In such cases, the anterior platform 60 would be removed and replaced with an anterior platform 60 having the desired sloping planes. Also, it will be understood that a flat plane 68 is provided on anterior platform 60 for those cases in which the patient has essentially no intercuspal engagement so that during movement of the lower jaw in a lateral direction, there is essentially no dropping of the lower jaw relative to the upper jaw.

It will be appreciated that in accordance with the present invention, there has been provided a dental jaw simulator which accurately duplicates the movement of the human jaw and, in particular, the lateral and downward movement of the lower human jaw.

A latitude of modification, change, and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein.

What is claimed is:

1. A dental jaw simulator for duplicating human jaw movements, comprising:
   a support frame,
   an upper jaw member pivotally mounted on said support frame for receiving an upper dental arch cast,
   a lower jaw member mounted on said support frame for receiving a lower dental arch cast, and
   means for moving said lower jaw member in protrusive and retrusive directions and in a lateral direction including a universal hinge arrangement in combination with an anterior platform mounted on said support frame and a forward pin member connected to said lower jaw member which engages and is movable relative to said anterior platform,
   said anterior platform including first and second sloping planes meeting at the center of said platform to form a crest and sloping downwardly from said crest to the edge of said platform, said forward pin member being movable on said first and second sloping planes to guide said lower jaw member to move downwardly and in a retrusive direction about said hinge arrangement so that as said lower jaw member is moved laterally, it drops downwardly and moves in an arc for duplicating the movements of the lower human jaw during lateral movement thereof.

2. A dental jaw simulator in accordance with claim 1, wherein said anterior platform includes a flat plane adjacent said sloping planes.

3. A dental jaw simulator in accordance with claim 2, wherein said sloping planes form an angle with said flat plane in the range of 0° to 30°.

4. A dental jaw simulator in accordance with claim 1, wherein said anterior platform includes a trough formed at said crest, said forward pin member being movable along said trough in the protrusive and retrusive directions.

5. A dental jaw simulator in accordance with claim 4, wherein said trough includes a recess formed therein for receiving the lower end of said forward pin member for establishing the occlusal position of said upper and lower jaw members.

6. A dental jaw simulator in accordance with claim 5, wherein the lower end of said forward pin member includes a spring-biased ball member engageable with said recess for establishing the rest position of said upper and lower teeth.

7. A dental jaw simulator in accordance with claim 1, wherein said anterior platform is removable from said support frame and is interchangeable with other anterior platforms having different sloping planes.

8. A dental jaw simulator in accordance with claim 1, wherein said anterior platform is movable and adjustable within guides formed on said support frame.

9. A dental jaw simulator in accordance with claim 1, wherein said forward pin member is adjustable relative to said lower jaw member.

10. A dental jaw simulator in accordance with claim 1, wherein the axis of said hinge arrangement is disposed above and behind said lower jaw member to duplicate the position of the temporomandibular joint relative to the lower human jaw.

11. A dental jaw simulator in accordance with claim 10, wherein the axis of said hinge arrangement is provided with locking means to prevent movement in one direction so that the occlusal position may be established.

12. A dental jaw simulator in accordance with claim 1, wherein said lower jaw member is supported on an L-shaped member connected to said hinge arrangement.

13. A dental jaw simulator in accordance with claim 1, wherein said upper and lower dental arch casts each include a tray member removably connected to said support frame so that said tray members are interchangeable with other tray members.

14. A dental jaw simulator in accordance with claim 13, wherein each of said tray members includes means for removably holding the mounting plaster of the dental arch cast within said tray member.

15. A dental jaw simulator in accordance with claim 14, wherein said means for removably holding said mounting plaster includes a sliding handle slidable through the walls of said tray member.

16. A dental jaw simulator in accordance with claim 14, wherein said tray member is formed of plastic.

17. A dental jaw simulator in accordance with claim 13, wherein said support frame includes removable locking means for removably connecting said tray member to said support frame.

18. A dental jaw simulator in accordance with claim 17, wherein said removable locking means is adjustable relative to said support frame.

* * * * *